United States Patent [19]

Green

[11] 4,010,251
[45] Mar. 1, 1977

[54] SCANNING AGENT COMPOSITION AND USE IN IMAGING LIVER AND FOR BILIARY FUNCTION

[76] Inventor: Allan M. Green, Cardinal Lane, Gates Mill, Ohio 44040

[22] Filed: Dec. 16, 1974

[21] Appl. No.: 533,109

[52] U.S. Cl. .............................. 424/1.5; 260/112 R
[51] Int. Cl.$^2$ .................. A61K 29/00; A61K 43/00
[58] Field of Search ........ 424/1; 260/112 R, 112.5, 260/113 R

[56] References Cited

OTHER PUBLICATIONS

Morell, et al., Journal of Biological Chemistry, vol. 246, No. 5, Mar. 10, 1971, pp. 1461–1467.
Gregoriadis, et al., Journal of Biological Chemistry, vol. 245, No. 21, Nov. 19, 1970, pp. 5833–5837.
Heusser, NSA, vol. 27, No. 9, May 15, 1973, Abstract No. 20200.
Lin, et al., NSA, vol. 30, No. 7, Oct. 15, 1974, Abstract No. 19055.
Wells, NSA, vol. 24, No. 1, Jan. 15, 1970, Abstract No. 773.

*Primary Examiner*—Benjamin R. Padgett
*Assistant Examiner*—Christine M. Nucker
*Attorney, Agent, or Firm*—Caesar, Rivise, Bernstein & Cohen

[57] ABSTRACT

A composition to be used in a method for imaging liver and for biliary function, the composition comprising a scanning agent that is combined with a radioisotope. The scanning agent is preferably a glycoprotein whose glycosidic side chains terminate in a sialic acid moiety followed by a galactose as exemplified by gamma globulin. The preferred radioisotope is technetium ($^{99m}$Tc).

The composition of the invention will bind to hepatocyte (liver cell) membranes whereas most known pertechnetated hepatic scanning agents attach to the reticuloendothelial cells of the liver (Kuppfer cells) with the advantage being that the present composition will be excreted into the bile ducts and make its way to the intestines, thus acting as an indicator of biliary tree patency.

The composition has been administered to human subjects and animals for liver imaging using the anger camera as well as for evaluating the biliary function.

15 Claims, No Drawings

SCANNING AGENT COMPOSITION AND USE IN IMAGING LIVER AND FOR BILIARY FUNCTION

This invention relates to a composition and method for visualizing the liver and for evaluating biliary function involving an altered glycoprotein or glycopeptide labelled with a radionuclide as an imaging agent.

The early period of radionuclide scanning saw the trial of numerous radiolabeled agents before current techniques became widely accepted. The experimental radiopharmaceuticals fell into two groups: Those metabolized by hepatic parenchymal cells (60percent of liver mass) and those phagocytixed by the reticuloendothelial (Kupffer) cells of the liver. (See McCready, V. Ralph, "Scintographic studies of space occupying liver disease." *Seminars in Nuclear Medicine*, 2 (1972) 108). The former group includes $^{131}$I-rose bengal, $^{131}$I-sodium iodipamide (RadioCholografin), $^{99}$Mo and $^{69m}$ZnCl; agents concentrated in the Kupffer cells include $^{99m}$Tc sulphur colloid, $^{131}$I-colloidal albumin, $^{98}$Au colloid and $^{113m}$In ferrous hydroxide. In addition, $^{67}$gallium citrate has recently gained favor as a radionuclide that concentrates in the liver, but prefers areas of inflammation and tumor. (See Lomas, F., P. E. Dibos andd H. N. Wagner, "Increased specificity of liver scanning with the use of $^{67}$gallium citrate." *New Eng. J. Med.*, 286 (1972) 1323).

Of the agents taken up by the hepatocytes, only $^{131}$I-rose bengal, a halogenated fluorescein dye, ever gained wide acceptance as a scanning agent. Unlike the colloidal material, rose bengal is extracted from the circulation by the hepatocytes, metabolized, secreted through the biliary system, concentrated in the gall bladder and excreted into the duodenum. (See Neurman, L., "On the distribution and kinetics of injected $^{131}$I-rose bengal." *Acta Med. Scand.: Suppl.* 354,1960). In addition to providing information about hepatic morphology, parenchymal function and patency of the biliary tree could be assessed by following movement of the dye into the gut. Disappearance of $^{131}$I-rose bengal from the circulation could also be evaluated as a measure of hepatic function.

Despite this advantage of allowing functional evaluation, rose bengal has fallen from favor because of several disadvantages. First, it takes about thirty (30) minutes for maximal concentration in the liver (normal patients have a 20:5 minutes ratio of blood $^{131}$I-rose bengal concentrations of 0.39 to 0.51). (See Nordyke, R. A., "Metabolic and physiologic aspects of $^{131}$I-rose bengal in studying liver function." *Seminars in Nuclear Medicine*, 2 (1972) 157). Within 20 minutes biliary excretion has begun, but scanning with a rectilinear scanner is too slow to avoid artifacts due to changing biliary and duodenal loop radioactivity. Even Anger scintillation camera imaging may show artifactual results. Secondly, $^{99m}$Tc has advantages over $^{131}$I for scanning including its low radiation dose to the patient per millicurie and its favorable gamma emission at 140 keV which is more suitable for the generally available imaging cameras. (See Kazem, I., P. Gelinsky and P. Schenck, "Organ visualization with Technetium $^{99m}$ preparations," *Brit. J. Radiology*, 40 (1967) 292). Finally, the low affinity of the liver for rose bengal has caused much difficulty in interpreting the results of scans obtained for the purpose of eliminating extrahepatic biliary obstruction as a possible diagnosis in difficult cases such as hepatitis with sufficient parenchymal edema to cause secondary obstruction of the biliary canaliculi. (See Gottschalk, A., "Liver Scanning." *J. Amer. Med. Assoc.*, 200 (1967) 150. The instant invention is far better for imaging because of its high affinity for hepatocyte membranes and its possible use of technetium $^{99m}$Tc as its radioactive principle.

Thus, the preferred liver scanning agents of the present invention is $^{99m}$Tc sulphur colloid. Depending on colloid size (see Dobson, E. G. and H. B. Jones, "The behavior of intravenously injected particulate material. Its rate of disappearance from the blood stream as a measure of liver blood flow." *Acta. Med. Scand.*, 144 (1952). Suppl. 273) this agent is taken up by reticuloendothelial cells of spleen and bone marrow as well as by Kupffer cells. This may have advantages in allowing spleen imaging and in assessing hepatic reticuloendothelial dysfunction. It may also have disadvantages in preventing accumulation of sufficient colloid in the liver to produce a clear image or by obscuring differentiation between a large left hepatic lobe and the spleen.

Ashwell and his colleagues have described the uptake of desialylated glycoproteins by receptors on the hepatic parenchymal cell plasma membrane (see Morell, A. G., G. Gregoriadis, H. I. Scheinberg, J. Hickman and G. Ashwell. "The role of sialic acid in determining the survival of glycoproteins in the circulation". *J. Biol. Chem.* 246 (1971) 1461) and by the catabolism of these altered glycoproteins by hepatic lysosomes. (See Gregoriadis, G., A. G. Morell, I. Sternliev and I. H. Scheinberg." Catabolism of desialylated ceruloplasmin in the liver." *J. Biol. Chem.* 245 (1970) 5833.

The instant invention involves the preparation and the use of desialylated glycoproteins and desialylated glycopeptides labelled with a radionuclide suitable for imaging and detection by currently available nuclear medicine equipment which would specifically be useful in the visualization of hepatic morphology and the evaluation of biliary function.

A particularly useful embodiment of the invention involves the preparation and use of $^{99m}$Tc-desialylated human gamma globulin ($^{99m}$Tc-DHGG) as a new, rapid and highly specific agent for liver imaging and for the evaluation of biliary function. While all of these agents are bound by liver cell membranes, the subsequent fate of the radiolabel may differ with each radionuclide. For example, while both $^{131}$I and $^{99m}$Tc labelled desialylated glycoproteins are rapidly cleared from the circulation and appear in the liver within minutes, $^{131}$I is cleaved from the desialylated glycoproteins after hepatocyte uptake and largely excreted through the kidneys. The $^{99m}$Tc label, however, is secreted through the biliary tree after metabolism by the hepatocytes and appears in the duodenum of rats within 40 minutes after injection. Thus, $^{99m}$Tc-DHGG can be used for functional studies of the biliary tract.

It can be seen that the invention involves a family of scanning agents composed of many glycoproteins and glycopeptides whose glycosidic side chains have been modified by desialylation so as to make them bind to receptors on the liver cell plasma membrane and which are chemically combined (i.e., labelled) with any of several radioisotopes suitable for clinical radionuclear scanning.

With previous liver scanning agents: there is no known agent that combines a technetium label with a material that bind to heptocyte (liver cell) membranes. The known pertechnetated agents bind to the reticuloendothelial cells of the liver (Kuppfer cells). This is an important distinction, since only the agents attaching to hepatocytes — there are two major types of liver cells: hepatocytes and Kuppfer cells — only agents binding to hepatocytes are excreted directly into the bile ducts and make their way to the intestines, thus acting as an efficient indicator of biliary tree patency. Colloidal materials phagocytized by the Kuppfer cells are generally referred over a long period on these cells. It is true that although glycoproteins have been modified so that they bind to liver cell membranes, they have never been combined with a radioactive label suitable for clinical scanning and have never been employed to such an end. In fact, certain radioactive labels ($^3$H and $^{14}$C) suitable for laboratory work have been attached to such modified proteins. This was done for other purposes entirely.

In fact, the embodiment of the invention using gamma globulin which had been desialylated would not have been expected to bind to the liver at all according to the prior literature. See the article by Kornfeld et al., which reports that gamma globulin modified in such a way does not, in fact, bind to liver cell membranes; and this was the conventional wisdom of the prior art.

The diseases in which the invention would be useful include:

differential diagnosis of right upper quadrant pain.
detection of malposition of the liver.
differential diagnosis of abdominal masses.
differentiation of parenchymal and obstructive liver disease.
preoperative and postoperative evaluation of patients with malignancies.
provision of objective data in evaluating the effect of anit-cancer chemotherapy on liver metastases and tumors and for evaluating the effect of radiotherapy.
location of vascular anamolies of the liver.
detection of primary carcinoma of the liver.
evaluation of liver function in infections and in serum hepatitis.
assessment of hepatic size.

By being cleared through biliary system of the liver to the common bile duct and then into the duodenum through the ampulla of Vater, the technetium embodiment of the scan enables the evaluation of biliary tract patency. In complete obstruction of the common duct — as by a pancreatic tumor or a gall stone — no scanning agent would be visualized in the duodenum. Partial obstruction would be indicated by a delay in visualization of the scanning agent in the bowel.

Among the radioisotopes suitable for hepatobiliary imaging that can be used in this invention are $^{125}$I$^{131}$I, $^{99m}$Tc.

As for the various glycoproteins and glycopeptides that can be used in the scanning agents, these would include any glycoproteins or glycopeptides whose glycosidic side chains terminate in a sialic acid moiety followed by a galactose. Specific examples of suitable proteins include gamma gloculin — a preferred embodiment because of its simple isolation without danger of hepatitis antigen contamination — chorionic orosomucoid, thyroxine-binding globulin, ceruloplasmin, human chorionic gonadotropin, thyroglobulin, fetuin, macroglobulin, haptoglobin, follicle-stimulating hormone, lactoferrin. In addition, glycopeptides prepared from these proteins by methods well known to those in the art (as for example that of Jamieson, G. A., *Journal of Biological Chemistry* 240, (1965) 2019, 2914) may be desialylated by enzymatic or chemical means and may also be used as scanning agents after labelling with an appropriate radioisotope. Alternatively, the protein may be labelled with a radioisotope prior to degradation and generation of the glycopeptides.

The critical elements of the scanning agent composition of this invention appear to be:

1. The protein or peptide must have a glycosidic residue.
2. The glycosidic residue must end in a sialic acid group and have a penultimate galactosyl group.
3. Some of the terminal sialic acids must be removed to expose the penultimate galactosyl residue.
4. The glycoprotein or glycopeptide must be labelled with a radioactive isotope which can be detected by scanning equipment, which emits gamma rays not harmful to the patient and which has a short half-life or rapid excretion so that the cumulative dose of radioactivity to the patient is safe.
5. The glycoprotein or glycopeptide must not be toxic in the species used.
6. The glycoprotein or glycopeptide must be able to be prepared free of hepatitis antigen contamination.
7. The scanning agent must be taken up by the liver fast enough so that it would be cleared from the circulation before it begins to appear in the bowel and obscure the image of the lower border of the liver.

The invention has now been used in humans. Human use requires the availability of sterile, non-pyrogenic hepatitis antigen-free material. Gamma globulin from human serum has been used which has been desialylated with incubation for 1 hour at 80° C in 0°1 N H$_2$SO$_4$ and then labelled with technetium. Alternatively, gamma globulin from human serum is used without prior treatment and altered during the pertechnetation procedure.

Sterility and pyrogenicity testing is performed. All operations are carried out under sterile conditions. An aliquot of the material containing 2 to 3 millicuries is injected intravenously — usually into the antecubital area. However, 1 to 10 millicuries may be injected. Photographs are then taken with an Anger photoscintillation camera in the anteroposterior, posteranterior and left lateral decubitus position; from 50,000 to 500,000 counts are collected for each Anger camera photograph.

MATERIALS AND METHODS

Thyroxine-binding globulin (TBG) from pooled human serum was purified by affinity chromatography as previously described. (See Pensky, J. and J. S. Marshall "Studies on thyroxine-binding globulin (TBG). II. Separation from human serum by affinity chromatography." *Arch. Biochem. Biophys.* 135 (1969) 304. Human gamma globulin (Cohn fraction II, Armour) were used as supplied by the manufacturer. Desialylated glycoproteins were prepared either by incubation with 0.1N H$_2$SO$_4$ for 1 hour at 80° C or by incubation for 24 hours at room temperature with V. Cholera neuraminidase (Behringwerke) 5 units per 100 ug protein in acetate buffer, pH 5.4, containing 5mM calcium chloride.

$^{99m}$Tc labelling was performed either according to the method of Persson and Liden. (See Persson, R. B. R. and K. Liden. "$^{99m}$Tc-labelled human serum albumin: A study of the labelling procedure" *Int. J. Appl. Rad. Isotopes.* 20 (1969( 241) or by electrolysis using power pack and Zirconium electrodes and applying 100 amps for 40 seconds. About 10mC $^{99m}$Tc was used per 40ug protein yielding specific activities of about 50uC/ug.

Binding of desialylated glycoproteins to rat liver plasma membrane in vitro was demonstrated by an inhibition assay described in Van Lenten and Ashwell (see Van Lenten, L. and G. Ashwell. "The binding of desialylated glycoproteins by plasma membranes of rat liver." *J. Biol. Chem.* 247 (1972) 4633 which was used previously. (See Marshall, J. S., A. M. Green, J. Pensky, S. Williams, A. Zinn and D. Carlson. "Measurement of circulating desialylated glycoproteins and correlation with hepatocellular damage." *J. Clin. Invest.* September 1974). This assay takes advantage of the ability of nonradioactive desialylated glycoproteins to compete for membrane binding with a standard amount of radiolabelled desialylated protein.

The ability of desialylated and native human and bovine gamma globulin to bind to liver cell plasma membranes is demonstrated by their ability to inhibit the binding of $^{131}$I-DTBG. Normal human gamma globulin (HGG) does not bind to any appreciable extent in concentrations of up to 100ug/ml. Untreated bovine gamma globulin (BGG) appears to show some inhibition; this may be due to the carbohydrate configuration of the protein, but is more likely secondary to desialylation that could occur during purification and storage.

After desialylation both HGG and BGG bind to the liver plasma membranes; however, they have less avidity than DTBG.

Adult male Wistur rats weighing about 400g and male New Zealand rabbits weighing about 2.5kg. were used in the in vivo animal imaging studies.

After intravenous injection of the labelled compounds (100–400uCi) as a bolus into experimental animals, hepatic imaging was performed on a Pho-Gamma III scintillation camera (Nuclear Chicago Corp., Des Plaines, Ill.) using a 140keV parallel collimator. Images were recorded on Polaroid type 55 film.

Imaging of a rat and rabbit liver after injection of $^{99m}$Tc-DHGG has thus been achieved. Secretion through the biliary system is noted by thirty (30) minutes post-injection. The control experiment in which $^{131}$I-HGG was injected shows that the label remains in the circulation after 48 hours. Interestingly, a control experiment in which native HGG was pertechnetated showed the same rapid uptake of the material by the liver as occurred with the $^{99m}$Tc-DHGG. Apparently, desialylation of the protein occurs spontaneously during the pertechnetation procedure in acid media.

Finally, the effect of biliary obstruction was observed by ligating the common bile duct of a rate under ether anaesthesia. This is shown in scintophotos produced by intravenous injection of 0.5mC $^{99m}$Tc-DHGG 5 minutes after ligation of the common bile duct. There is apparently an immediate effect upon hepatic uptake of the tracer; and radionuclide fails to localize in the liver even after 1 hour post-injection. However, scintophotos of the same animal taken 18 hours post-injection show good hepatic morphology and the existence of a concentration of tracer caudal to the liver. Significantly, no radioactivity is seen in the intestine. Thus, the presence of complete biliary obstruction can be indicated by delayed tracer uptake and the failure of radioactivity to appear in the intestine; moreover, good hepatic morphology can still be visualized in delayed films.

After approval by the appropriate institutional committee on human investigation and the completion of proper patient consent forms, human subjects were studied at University Hospital, Cleveland, Oh. Liver scans were performed using technetium $^{99m}$Tc desialylated human gammma globulin. A 3mCi dose provided prompt and efficacious hepatic visualization.

Radiolabelled desialylated thyroxine-binding globulin (DTBG) has also been prepared and has been found to be effective as a liver imaging agent after intravenous injection.

Studies with desialylated TBG have previously shown the compound to have a half-life of about 4–5 minutes in the circulation. (See Refetoff, S., V. S. Fang and J. S. Marshall. "Chemical and biological properties of purified native and desialylated human thyroxine binding globulin." Submitted for publication.) $^{131}$I-DTBG and $^{131}$I-DHGG are rapidly taken up by the hepatocytes, and clearance of the iodine label by the kidneys is noted by 20 or 30 minutes post-injection. Thus, while time available for hepatic imaging is limited after intravenous injection, exposure of the patient to radioactivity using this embodiment of the instant invention is minimal.

The $^{99m}$Tc labelled desialylated molecules are taken up by the liver as rapidly as the iodinated analogues. However, the label remains in the liver in the animal with biliary obstruction. In the normal rat and rabbit, biliary secretion into the duodenun can be visualized by the Anger camera 30 to 40 minutes post-injection. Thus, like $^{131}$I rose bengal, these pertechnetated compounds offer a method of studying hepatobiliary secretory function as well as the morphology and patency of the biliary tree. However, $^{99m}$Tc-desialylated glycoproteins offer an agent which is cleared from the circulation into the liver at least 5 times faster than rose bengal so that imaging can begin soon after injection and well before biliary secretion obscures hepatic morphology. The use of $^{99m}$Tc is also a significant advantage over $^{131}$I because of its high counting rate, an easily collimated 140keV gamma emission and a minimum of patient irradiation. (See Gottschalk, A., "Liver Scanning". *J. Amer. Med. Assoc.*, 200 (1967) 150).

Through the embodiment of this invention as the technetium $^{99m}$Tc - DHGG, there are many advantages as applied to human use. DHGG is easily purified free of hepatitis contamination and is already available in a pharmaceutical preparation suitable for human use. Although the molecular composition exhibits microheterogeneity, human gamma globulin typically contains one carbohydrate moiety in the Fc portion of each heavy chain; and each glycosidic group contains zero to two moles of sialic acid with a penultimate galactosyl residue. (See Kornfeld, R., J. Keller, J. Baenziger and S. Kornfeld. "The structure of the glycopeptide of human gamma G myeloma proteins." *J. Bio. Chem.* 246 (1971) 3259). Thus, the typical gamma globulin molecule contains two moles of sialic acid; and the work reported here demonstrates that desialylation leads to binding of the molecule to liver membranes in vitro and in vivo.

Pertechnetation at acid pH in the presence of FeCl$_3$ catalyst or Zirconium electrodes as employed here apparently desialylates gamma globulin. This is indicated by the observation that $^{99m}$Tc-HGG, $^{99m}$Tc-DHGG and $^{131}$I-DHGG behave identically with uptake and concentration in the liver while $^{131}$I-HGG is not concentrated in the liver. The pertechnetation procedure is apparently analogous to periodate treatment of glycoproteins at acid pH, a standard method of sialic acid removal as a first step in glycosidic degradation. (See Neuberger, A. and R. D. Marshall. Structural analysis of the carbohydrate group of glycoproteins in *Glycoproteins: Their Composition, Structure and Function*. A Gottschalk, ed. Elsevier Publishing Company, Amsterdam 1966, p. 246. The pertechnetation procedures used here obviate the necessity for prior enzymatic or chemical treatment with neuraminidase or 0.1N $H_2SO_4$; procedures for carrying out protein pertechnetation with pyrogen-free sterile materials for human use are already well established and readily available.

Radiolabelled desialylated glycoproteins and radiolabelled desialylated glycopeptides appear to provide potentially powerful new agents for radioisotope liver scanning.

USE WITH HUMANS $^{99m}$Tc-labelled human gamma globulin was administered ($^{99m}$Tc-HGG) to human subjects after appropriate committee approval and patient consent was obtained for the purpose of evaluating the usefulness of this agent in liver imaging using the Anger camera. The component $^{99m}$Tc radionuclide, the immune human globulin and the radiolabelling procedure all have FDA approval for use in humans. Animal studies in our laboratory using two species have demonstrated the efficacy and safety of this procedure.

The study described here demonstrated the advantages of this agent over currently available scanning materials and the practicality of its use.

The potential dangers are nominal. FDA-approved, commercially available components and procedures are used throughout. Of course, aseptic technique should be enforced in the laboratory used for the preparation of radiolabelled proteins for human administration.

The dose of radioactivity administered was one to threee millicuries, the amount currently used for liver scanning. In fact, in all patients with biliary tract patency, the radiation dose to the liver was reduced from present levels since the material is rapidly excreted from the hepatocytes whereas the currently used $^{99m}$Tc-sulfur colloid remains in the reitculoendothelial cells indefinitely. A 3mCi dose of $^{99m}$Tc-sulfur colloid is estimated by the manufacturer to be 90% concentrated in the liver and to deliver a dose of 1.0 rad to the liver. This compares favorably with the dose of 6.4 rads delivered by the alternative scanning agent $^{198}$Au-colloid and 4.0 rads with $^{131}$I-rose bengal. The half-life of $^{99m}$Tc is six hours and no particular precautions concerning its excretion need be taken; only 6.25% of the initial activity is present after 24 hours. Imaging apparatus already in routine use is employed in the application of the instant invention.

PREPARATION OF ONE EMBODIMENT

Unlabelled human gamma globulin is readily available from the pharmacy; the reasons for its selection have been outlined above. Using the method of Persson and Liden (*Int. J. Appl. Rad. Isotopes*, 20 (1969) 241) 50ug of protein is added to 2 – 10 ml of eluate from a $^{99m}$Tc generator containing 10 to 100 mC in solution with 0.5ml 0.2M ascorbic acid and 0.5ml 0.1M FeCl$_3$ 6H$_2$) after mixing and adjustment of the pH to 7.4 with sterile 0.15M NaOH. The pH is then adjusted to 2.4 – 2.0 with 0.15M HCL and stirred for 15 minutes. $^{99m}$Tc-HGG is purified by elution through a Dowex 1 1 × 8 column with sterile 0.15M NaCl and the pH is adjusted to 6.8 with 0.15M NaOH or 0.15M Na$_2$CO$_3$. Terminal sterilization is carried out by passage of the $^{99m}$Tc-HGG through a 0.22 u millipore filter. Bacterial culturing is done routinely as a part of the evaluation of suitability for human use. Pyrogen testing must also be done on all materials used in this procedure.

ALTERNATE PREPARATION METHODS

The first alternate preparation method involves 50ug to 100ug of protein in aqueous solution at pH 2 to pH 7 to which 2 – 10ml of eluate from a $^{99m}$Tc generation is added containing 10 – 100mCi $^{99m}$Tc. A zirconium electrode is then inserted on the incubation vial through which a small current (50 – 150 amperes) is passed, with the current then passing through the protein for 10 seconds to 1 minute in the presence of a ferric catalyst. A small amount of zirconium will go into solution to act as a catalyst. This preparation method will avoid the purification step i.e., terminal elution.

Another preparation method involves the use of 1 – 10mg stannous chloride in solution with 50mg to 100mg of protein in aqueous solution at pH 2.2 to 3.2 to which 2 – 10ml of eluate from a $^{99m}$Tc generator containing 10 – 100 mCi of $^{99m}$Tc is added.

CLINICAL STUDY

Patients in the study were scheduled for routine liver scanning at the request of their attending physician and had been studied for biliary obstruction by radiologic and clinical tests. Evaluation with $^{99m}$Tc-DHGG was made only after routine liver scanning had been performed.

Basically, the tests with $^{99m}$Tc-DHGG consisted of injecting 1 – 3mCi of radiolabelled agent intravenously and determining (a) clearance of the label from the blood by means of a probe scintillation counter such as that used in thyroid uptake studies positioned against the head, (b) uptake of the label by the liver as visualized by Anger camera photoscintillation imaging, and (c) excretion of the label into the intestine as determined by Anger camera techniques. The data obtained allowed statements to be made about the anatomical status of the liver and about the functional status of the heptobiliary system.

A 10ml blood sample was drawn the morning of the examination for determination in the laboratory of levels of circulating desialylated glycoproteins.

The patient was brought to Nuclear Medicine following a complete fast from midnight the day before the test. A collimated scintillation probe was placed against the left lateral aspect of the head centered at the ear, and a background count was recorded. With the patient supine and the Anger camera positioned for an AP scintiphoto, 1.0 to 3mCi of $^{99m}$Tc-DHGG in 1 to 5cc isotonic saline was injected intravenously in the antecubital fossa.

The counting rate of the collimated probe was then continuously recorded with time. Anger scintiphotos began when 95% of the initial activity had disappeared into the liver from the circulation—estimated to take between 5 and 10 minutes—or at 20 minutes post injection. Four views were obtained: Anteroposterior (AP), right and left lateral, and posteroanterior (PA), using 3mCi yields the desired 500,000 counts per picture in about 1 minute. Oblique views were added as needed.

To determine biliary tract patency, an additional AP view was taken at 60 minutes and again after the administration of 200 to 300cc of whole milk as a cholecystogogue.

Every patient was evaluated to
1. Compare information obtained from his standard liver scan with the scan performed using $^{99m}$Tc-HGG using a double-blind technique.
2. To correlate the rate of clearance of $^{99m}$Tc-HGG from the circulation with the nature and degree of his hepatobiliary impairment provided by chemical, clinical and surgical studies performed during his hospital stay.

Specifically, $^{99m}$Tc-DHGG was evaluated for its sensitivity and accuracy in defining hepatic filling defects the radioisotope being suitable for hepatobiliary imaging. Also evaluated was the imaging produced by the agent in cirrhosis in whom decreased hepatic mass and hepatic blood flow shunt $^{99m}$Tc-HGG indifferentiating extrinsic intrinsic biliary obstruction. In addition, the level of circulating desialylated glycoproteins was evaluated as a measure of hepatic function and as a predictor of $^{99m}$Tc-HGG scanning utility.

From the foregoing, it is clear that the present invention was the result of a search for improved liver scanning agents which would take advantage of physiologic properties of the liver other than the colloidal uptake of particulate material by Kuppfer cells and the uptake of aromatic dyes utilized by the prior art. The invention evolved from a theory that a specific biochemical action of the liver cell might be found that could be used to advantage in the design of specific scanning agents. The recent work detailing the ability of the liver to take up glycoproteins with altered glycosidic side chains seemed to offer a hepatic function which could be used to such an advantage. Through experimental trial and error, radiolabelled desialylated glycoproteins were compounded and it was discovered how they were taken up and how each label was handled by the liver. Thus, it was found that while iodine was cleaved by the hepatocytes and secreted back into the circulation for excretion by the kidneys, technetium label remained with the agent or degradation products that were secreted through the biliary tree. Because of the benefits of gamma globulin — plentiful supply, freedom from hepatitis antigen — its behavior was investigated although reports had appeared in the literature claiming it did not bind to liver cells after desialylation. These experimental results showed that it was, in fact, a suitable agent; and is one of the preferred embodiments of the invention.

Without further elaboration, the foregoing will so fully illustrate my invention that others may, by applying current or future knowledge, readily adapt the same for use under various conditions of service.

What is claimed as the invention is:
1. A scanning agent composition comprising glycoproteins and glycopeptides having glycosidic side chains terminating in a sialic acid moiety followed by a galactose, said glycoproteins and glycopeptides having been desialylated and chemically combined with a compatible radioisotope suitable for hepatobiliary imaging.
2. The composition of claim 1 wherein the glycoprotein is gamma globulin.
3. The composition of claim 1 wherein the radioisotope is $^{99m}$Tc.
4. The composition of claim 1 wherein the radioisotope is selected from the group consisting of $^{111}$In, $^{113m}$In, $^{131}$I and $^{99m}$
5. The composition of claim 1 wherein the glycoprotein is gamma globulin and the radioisotope is $^{99m}$Tc.
6. In a method for imaging liver comprising injecting an effective amount of a scanning agent composition comprising glycoproteins and glycopeptides having glycosidic side chains terminating in a sialic acid moiety followed by a galactose, said glycoproteins and glycopeptides having been desialylated and chemically combined with a compatible radioisotope suitable for hepatobiliary imaging.
7. The method of claim 6 wherein the glycoprotein is gamma globulin.
8. The method of claim 6 wherein the radioisotope is $^{99m}$Tc.
9. The method of claim 6 wherein the glycoprotein is selected from the group consisting of $^{111}$In, $^{113m}$In, $^{131}$I, and $^{99m}$Tc.
10. The method of claim 6 wherein the glycoprotein is gamma globulin and the radioisotope is 99mTc.
11. In a method for determining biliary function comprising injecting an effective amount of a scanning composition comprising glycoproteins and glycopeptides having glycosidic side chains terminating in a sialic acid moiety followed by a glactose, said glycoproteins and glycopeptides having been desialylated and chemically combined with a compatible radioisotope suitable for hepatobiliary imaging.
12. The method of claim 11 wherein the glycoprotein is gamma globulin.
13. The method of claim 11 wherein the radioisotope is $^{99m}$Tc.
14. The method of claim 11 wherein the glycoprotein is gamma globulin and the radioisotope is $^{99m}$Tc.
15. The method of claim 11 wherein the glycoprotein is orosomucoid and the radioisotope is $^{99m}$Tc.

* * * * *